United States Patent [19]

Abou-Gharbia et al.

[11] Patent Number: 4,675,403
[45] Date of Patent: Jun. 23, 1987

[54] 3-AMINOALKYL DERIVATIVES OF 5,5-DISUBSTITUTED HYDANTOINS WITH PSYCHOTROPIC ACTIVITY

[75] Inventors: Magid A. Abou-Gharbia, Wilmington, Del.; Gary P. Stack, Merion, Pa.

[73] Assignee: American Home Products Corporation, New York, N.Y.

[21] Appl. No.: 787,358

[22] Filed: Oct. 16, 1985

[51] Int. Cl.⁴ .................. C07D 403/14; C07D 401/14
[52] U.S. Cl. ................................. 544/230; 544/295; 544/364; 544/370; 546/15; 546/210
[58] Field of Search ............... 544/230, 295, 364, 370; 546/210, 15

[56] References Cited

U.S. PATENT DOCUMENTS 4,367,335 1/1983 Temple, Jr. et al. ............... 544/295

OTHER PUBLICATIONS

Zejc, "Chemical Abstracts", vol. 70, 1969, col. 37780a.
Cross, "Chemical Abstracts," vol. 78, 1973, col. 159666.
Polish J. Pharmacol. Pharm., 32, 173 (1980).
Arch. Immunol. Ther. Exp., 25, 291 (1975).

Primary Examiner—Glennon H. Hollrah
Assistant Examiner—James H. Turnipseed
Attorney, Agent, or Firm—George Tarnowski

[57] ABSTRACT

There are disclosed compounds of the formula

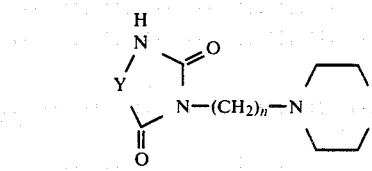

wherein
Y represents

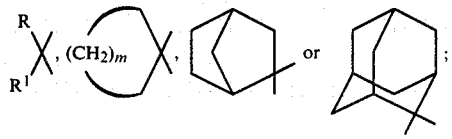

R and R¹ are each, independently, hydrogen, lower alkyl, phenyl or naphthyl, with that proviso that when R and R¹ are both phenyl, R² is other than phenyl;
Z is

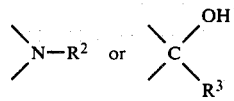

$R^2$ is 2-pyrimidinyl, halopyrimidin-2-yl, 2-pyridinyl, halopyridin-2-yl, cyanopyridin-2-yl, phenyl or phenyl substituted with lower alkyl, halo or trifluoromethyl;
$R^3$ is phenyl or phenyl substituted with halo or trifluoromethyl;
m is 2-7;
n is 2-5; and and the pharmaceutically acceptable salts thereof and their use as antipsychotic/anxiolytic agents having a low liability for extrapyramidal side effects.

10 Claims, No Drawings

3-AMINOALKYL DERIVATIVES OF 5,5-DISUBSTITUTED HYDANTOINS WITH PSYCHOTROPIC ACTIVITY

This invention relates to novel compounds having antipsychotic activity and being characterized by the general formula

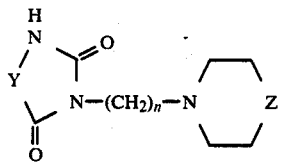

wherein
Y represents

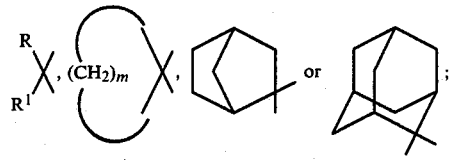

R and $R^1$ are each, independently, hydrogen, lower alkyl, phenyl or naphthyl, with that proviso that when R and $R^1$ are both phenyl, $R^2$ is other than phenyl;
Z is

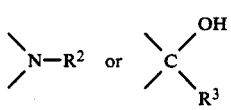

$R^2$ is 2-pyrimidinyl, halopyrimidin-2-yl, 2-pyridinyl, halopyridin-2-yl, cyanopyridin-2-yl, phenyl or phenyl substituted with lower alkyl, halo or trifluoromethyl;
$R^3$ is phenyl or phenyl substituted with halo or trifluoromethyl;
m is 2–7;
n is 2–5; and
the pharmacologically acceptable salts thereof.

The term "lower alkyl" refers to moieties having 1–6 carbon atoms in the carbon chain. The term "halo" refers to fluoro, chloro and bromo.

The compounds of the invention can form pharmaceutically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods. Thus, for example, an appropriately substituted 2,4-imidazolidinedione may be reacted with a suitable dihalo lower alkane in the presence of a strong base, such as sodium hydride, to yield an intermediate product:

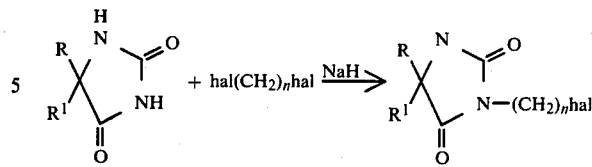

This intermediate product can then be reacted with, for example, an appropriately substituted 4-piperazine (or substituted-4-hydroxy piperidine) to yield the desired final product:

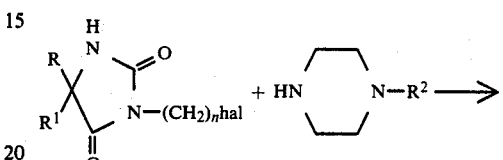

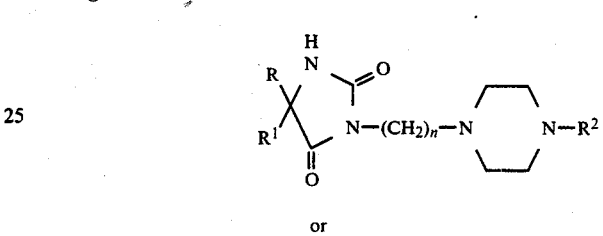

or

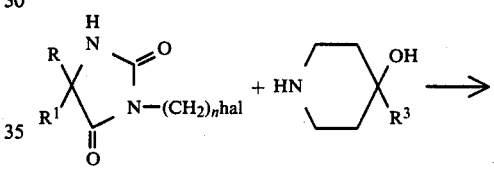

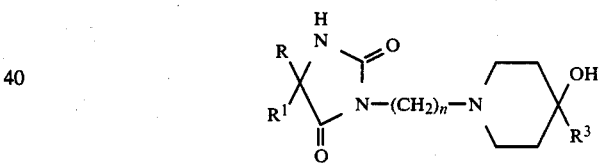

In the above sequences, R, $R^1$, $R^2$, $R^3$ and n are as defined hereinbefore and hal is a halo atom, such as chloro or bromo.

An alternative preparative sequence for compounds in which R and $R^1$ are taken together to form a ring system begins with the preparation of the N-carboxy-α-amino acid anhydride, as for example where Y forms a norbornane ring, by reacting the appropriate amino acid with phosgene or diphosgene:

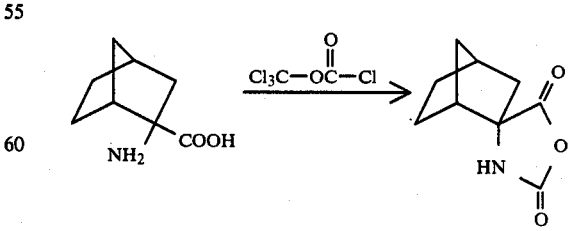

This intermediate anhydride is then subject to aminolysis with the desired ω-piperazinyl- or piperidinylalkylamine to form the corresponding α-amino acid amide:

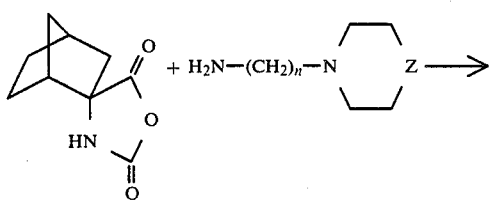

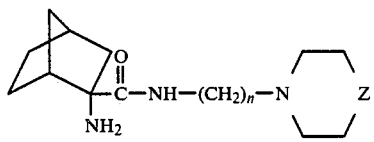

The α-amino acid amide is then cyclized upon treatment with diphosgene in the presence of triethylamine to form the desired final product spiro-hydantoin:

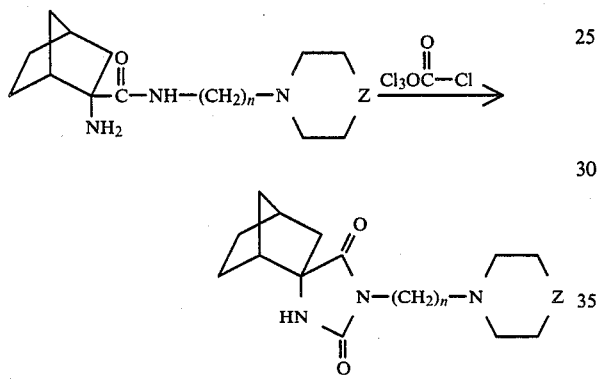

Compounds of the invention in which Y represents the moiety

can be prepared by condensation of the appropriate carbobenzoxy-α-amino acid with the desired ω-piperazinyl- or piperidinylalkylamine, in the presence of, for example, diisopropyl carbodiimide (DIC) and hydroxybenztriazole (HOBT) to form an intermediate amide:

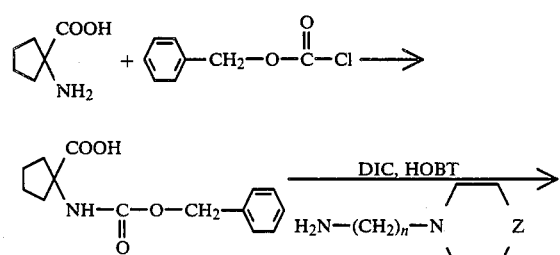

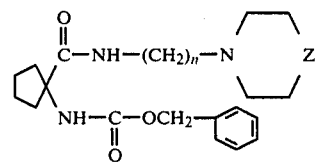

The intermediate amide may also be prepared in stepwise fashion via condensation of the appropriate carbobenzoxy-α-amino acid with an ω-hydroxy-alkylamine and protection of the resulting hydroxy group-containing compound with a conventional leaving group, e.g. methanesulfonyl chloride:

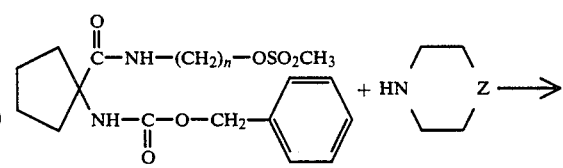

The leaving group is then displaced with the desired substituted piperazine or piperidine:

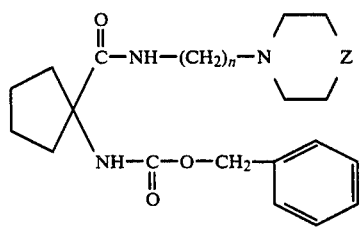

In the final step, the intermediate amide, prepared by either of the alternative schemes, is treated with sodium methoxide in refluxing methanol to obtained the desired final product, the substituted spirohydantoin:

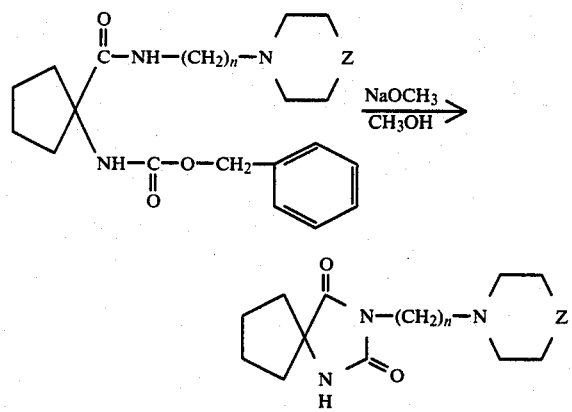

Of course, other methods of preparation, which will occur to those skilled in the art, may also be employed to prepare the compounds of the invention.

The starting materials used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl-butyl]-8-azaspiro[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display preclinical antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses (in mg/kg/day), the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

5,5-Diphenyl-3-[4-[4-(2-pyrimidinyl)-4-piperazinyl]-butyl]-2,4-imidazolidinedione, dihydrochloride To a stirred solution of 0.5 g (0.02 mol) of 5,5-diphenylhydantoin in 50 mL of dimethylformamide is added 0.6 g (0.03 mol) of sodium hydride and 3 g (0.02 mol) of 1-bromo-4-chlorobutane. The reaction mixture is stirred for 48 hours, then dimethylformamide is removed under reduced pressure and the remaining solid is extracted with methylene chloride ($3 \times 300$ mL).

The methylene chloride extract is dried over anhydrous $Na_2SO_4$ and evaporated under reduced pressure. The waxy solid (5 g; 74% yield) which separates is identified by IR and NMR and spectral data to be consistent with 5,5-diphenyl-3-[4-chlorobutyl]-2,4-imidazolidinedione. The title compound is prepared by dissolving 4 g (0.01 mol) of 5,5-diphenyl-3-[4-chlorobutyl]2,4-imazolidinedione in 60 mL of dimethylformamide. To this solution is added 6 mL of triethylamine and 1.6 g (0.01 mol) of 1-(2-pyrimidinyl)piperazine. The reaction mixture is stirred at room temperature for 48 hours. Dimethylformamide is removed under reduced pressure and the remaining solid is dissolved in water (30 mL) and extracted with methylene chloride ($3 \times 300$ mL). The methylene chloride extract is dried over anhydrous $Na_2SO_4$ and evaporated under reduced pressure to afford 3 g (64%yield) of a yellow oil which is converted to the dihydrochloride by dissolving in ethanol and adding ether saturated with hydrogen chloride; m.p. 170°–180° C.

Analysis for: $C_{27}H_3N_6O_2.2HCl$: Calculated: C, 59.66; H, 5.89; N, 15.46; Cl, 13.07; Found: C, 59.34; H, 5.49; N, 15.14; Cl, 13.06

EXAMPLE 2

1-[4-[4-(2-Pyrimidinyl)-1-piperazinyl]butyl]spiro[bicyclo[2.2.1]heptane-2,4'-imidazolidine]-2',5'-dione, dihydrochloride 2-Amino-2-norbornanecarboxylic acid hemihydrate (2.5 g; 0.02 mol) is suspended in 70 mL of dioxane. To this stirred suspension is added 6 mL of trichloromethylchloroformate (TCF) and stirring is continued for 4 hours at 55° C. or until a clear solution is obtained (reaction time from 4 to 6 hours). Dioxane is evaporated under reduced pressure and the separated solid is analyzed by IR and NMR to be spirobicyclo[2.2.1]heptane-2,4'-oxazolidine-2,5'-dione. This compound is dissolved in 50 mL of methylene chloride and to the stirred solution is added 4.7 g (0.02 mol) of 1-(4-aminobutyl)4-(2-pyrimidinyl)piperazine and stirring is continuted for 3 hours at 50° C.

The methylene chloride layer is washed with water, dried over anhydrous $Na_2SO_4$ and evaporated under reduced pressure to afford 2 g of 2-amino-2-bicyclo[2.2.1]heptyl-N-[4-[4-(2-pyrimidinyl)piperazinyl]acetanilide. The title compound is prepared by dissolving 2 g of 2-amino-2-bicyclo[2.2.1]heptyl-N-[4[4-(2-pyrimidinyl)piperazinyl acetanilide in 50 mL of methylene chloride, and to the stirred solution is added 4 mL of triethylamine and 4 mL of trichlormethylchloroformate. Stirring is continued at room temperature for 24 hours and the methylene chloride is washed with water, dried and evaporated under reduced pressure. The remaining solid, mp. 114°–116° C., is converted to the dihydrochloride; mp. 155°–158° C.

Analysis for: $C_{21}H_{30}N_6O_2.2HCl$: Calculated: C, 53.50; H, 6.79; N, 17.83; Found: C, 53.51; H, 6.93; N, 17.43

EXAMPLE 3

3-[4-[4-(2-Pyrimidinyl)-1-piperazinyl]butyl]-2,4-imidazolidinedione, dihydrochloride The title compound is prepared following the procedure of Example 1, using hydantoin instead of 5,5-diphenylhydantoin. The dihydrochloride salt (mp. 220°–222° C.) is isolated.

Analysis for: $C_{15}H_{22}N_6O_2 . 2HCl$: Calculated: C, 46.04; H, 6.14; N, 21.48; Cl, 18.16; Found: C, 45.59; H, 6.23; N, 21.15; Cl, 17.56

EXAMPLE 4

5,5-Pentamethylene-3-[4-[4-(2-pyrimidinyl)-4-piperazinyl]butyl]-2,4-imidazolidinedione, dihydrochloride The title compound is prepared following the procedure of Example 2 using 1-amino-1-cyclohexanecarboxylic acid instead of 2-amino-2-norbornanecarboxylic acid hemihydrate, with the compound being converted to the dihydrochloride, dihydrate; mp. 170°–174° C.

Analysis for: $C_{20}H_{30}ClN_6O_2.2HCl.2H_2O$: Calculated: C, 48.48; H, 7.27; N, 16.97; Found: C, 48.06; H, 7.24; N, 16.69

EXAMPLE 5

5,5-Dimethyl-3-[4-[4-(2-pyrimidinyl)-4-piperazinyl]butyl]-2,4-imidazolidinedione, hydrochloride To a stirred solution of 6.4 g (0.05 mol) of 5,5-dimethylhydantoin in 200 mL of tetrahydrofuran at 0° C. under nitrogen is added 50 ml of 1.0M sodium bis (trimethylsilyl)amide in tetrahydrofuran. After stirring the solution at 0° for 30 minutes, 17.1 g (0.10 mole) of 1-bromo-4-chlorobutane is added and stirring is continued at room temperature for 24 hours. The mixture is diluted to 1 liter with ether, washed with 500 ml each 2N HCl, saturated sodium bicarbonate solution, saturated brine and dried over sodium sulfate. After filtration, evaporation in vacuo, and trituration with hexane, 10.8 g of white solid (m.p. 51°–4°) is obtained, the NMR and IR of which are consistent with 5,5-dimethyl-3-[4-chlorobutyl]-2,4-imidazolidinedione.

The title compound is prepared by combining 2.2 g (0.010 mole) of the 5,5-dimethyl-3-[4-chlorobutyl]-2-4-imidazolidinedione prepared above, 2.5 g (0.015 mole) of triethylamine and 7.5 g (0.050 mole) of sodium iodide in 100 ml of dimethylformamide and heating at 80° under nitrogen for 24 hours. The solvent is then removed in vacuo and replaced with 300 ml of methylene chloride. This is washed thoroughly with water and with saturated brine and dried over $Na_2SO_4$. After filtration and evaporation in vacuo, the residue is column chromatographed on 200 g silica gel with 10% ethanol in chloroform as eluent. The crude product is converted to the hydrochoride by dissolving it in isopropanol, adding 3N isopropanolic HCl and then ether to yield 3.6 g of white solid, m.p. 195°–6°.

Analysis for: $C_{17}H_{27}N_6O_2Cl$: Calculated: C, 53.32; H, 7.11; N, 21.95; Found: C, 53.34; H, 6.98; N, 21.59

EXAMPLE 6

5,5-Dimethyl-3-[4-[4-(4-chlorophenyl)-4-hydroxy-1-piperidinyl]]butyl]2,4-imidazolidinedione, hydrochloride, hemihydrate 2.2 g (0.010 mole) of 5,5-dimethyl-3-[4-chlorobutyl]-2,4-imidazolidinedione, 2.1 g (0.010 mole) of 4-(4-chlorophenyl)-4-hydroxypiperidine, 1.0 g (0.010 mole) of triethylamine and 7.5 g (0.050 mole) of sodium iodide are combined in 100 ml dimethylformamide at 80° under nitrogen for 24 hours. Workup as in Example 5 provides 3.9 g of the title compound, m.p. 242°–3° C.

Analysis for: $C_{20}H_{29}N_3O_3Cl_2.\frac{1}{2}H_2O$: Calculated: C, 54.47; H, 6.88; N, 9.56; Found: C, 54.03; H, 6.84; N, 9.32

EXAMPLE 7

5,5-Tetramethylene-3-[4-[4-(2-pyrimidinyl)-4-piperazinyl]butyl]-2,4-imidazolidinedione, dihydrochloride To a stirred suspension of 12.9 g (0.010 mole) of 1-amino-1-cyclopentane carboxylic acid in 500 ml of methylene chloride is added 25 ml (0.10 mole) of N,O-bis(trimethylsilyl)acetamide. The mixture is stoppered and stirred at room temperature for 3 days, whereupon complete solution is obtained. 17 g (0.10 mole) of benzylchloroformate is added and the mixture stirred for an additional 1 hour. It is then washed with 300 ml each 2N HCl, water and saturated brine and dried over sodium sulfate. Filtration, evaporation and trituration with hexane gives 24 g of 1-carbobenzoxyamino-1-cyclopentane carboxylic acid, mp. 93°–5° C. 5.3 g (0.020 mole) of 1-carbobenzoxyamino-1-cyclopentane carboxylic acid is dissolved in 100 ml dimethylformamide and 3.1 g (0.020 mole) of 1-hydroxybenzotriazole hydrate and 2.5 g (0.020 mole) of 1,3-diisopropylcarbodiimide are added. The mixture is stirred at room temperature for three hours and 1.8 g (0.020 mole) of 4-amino-1-butanol is added. Stirring at room temperature is continued for 24 hours. The solvent is removed in vacuo and replaced with 500 ml of methylene chloride. The mixture is washed with 2N HCl, saturated sodium bicarbonate solution and water and dried over sodium sulfate. Filtration and evaporation gives 6.7 g of 1-carbobenzoxyamino-1-cyclopentane carboxylic acid, 4-hydroxybutylamide, m.p 117°–8° C.

To prepare the title compound, 3.3 g (0.010 mole) of the above amide is dissolved in 100 ml of methylene chloride and 1.1 g (0.011 mole) of triethylamine and 1.3 g (0.011 mole) of methanesulfonyl chloride are added. After stirring for one hour at room temperature, the mixture is washed with 50 ml portions of 2N HCl, saturated sodium bicarbonate and saturated brine, dried over $Na_2SO_4$, filtered and evaporated. The residue is combined with 2.5 g (0.015 mol) of 1-(2-pyrimidinyl)-piperazine, 1.5 g (0.015 mole) of triethylamine and 7.5 g (0.050 mole) of sodium iodide in 100 ml of dimethylformamide and heated at 80° under nitrogen for 24 hours. The solvent is removed in vacuo and the residue worked up as in Example 5. Two hours' treatment with sodium methoxide in refluxing methanol, followed by conversion to the hydrochloride gives the title compound, m.p. 233°–4° C.

Analysis for: $C_{19}H_{29}N_6O_2Cl$: Calculated: C, 55.81; H, 7.15; N, 20.55; Found: C, 55.47; H, 7.28; N, 20.20

EXAMPLE 8

5,5-Tetramethylene-3-[4-[4-(4-chlorophenyl)-4-hydroxy-1-piperazinyl]butyl]-2,4-imidazolidinedione, dihydrochloride 3.3 g (0.010 mole) of the 4-hydroxybutyl amide described in Example 7 is again converted to the mesylate by treatment with methanesulfonyl chloride/triethylamine in methylene chloride. The crude mesylate is combined with 2.1 g (0.010 mole) of 4-(4-chlorophenyl)-4-hydroxypiperidine, 1.0 g (0.010 mole) of triethylamine and 7.5 g (0.050 mole) of sodium iodide in 100 ml of dimethylformamide and heated at 80° under nitrogen for 24 hours. Workup as in Example 5 followed by a two hour treatment with sodium methoxide in refluxing methanol and conversion to the hydrochloride gives the title compound, m.p. 239°–40°.

Analysis for: $C_{22}H_{31}N_3O_3Cl_2$: Calculated: C, 51.65; H, 6.85; N, 9.21; Found: C, 57.66; H, 6.84; N, 8.86

EXAMPLE 9

The compounds of the invention are tested in an assay to determine their ability to antagonise apomorphine-induced stereotyped behavior. The assay measures the in vivo dopamine reception blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80® in water, are administered at several dose levels to male mice (6/dose level). A control group, run simultaneously with drug groups, receives equal volumes of solvent. Thirty minutes later (i.p. administration) or 60 minutes later (p.o. administration), drug-treated and control mice are challenged with 10 mg/kg apormorphine s.c.. Five minutes after the injection, the rearing-head-bobbing, licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| STANDARD COMPOUNDS: $ED_{50}$ and 95% confidence interval, mg/kg | |
|---|---|
| | intraperitoneal |
| Haloperidol | 1.37 (0.88–2.34) |
| Chloropromazine | 8.48 (4.79–16.38) |
| Clozapine | 30.06 (19.42–48.21) |

The compounds of the invention, when tested in this assay are inactive, evidencing a low potential for exhibiting extrapyramidal side effects, such as pseudo parkinsonism, tardive dyskinesia and the like.

EXAMPLE 10

The compounds of the invention are further studied for their ability to inhibit limbic D-2 dopamine receptor binding. This in vitro assay measures the ability of the compounds tested to bind to the dopamine receptor sites. Those compounds which exhibit a weak binding effect have a low liability to display potential extrapyramidal side effects.

The test is carried out as follows:

Several rats are decapitated and the brains are rapidly removed. Limbic brain tissue (nucleus accumbens, septal area, olfactory tubercle) is dissected and homoganized on ice in 9 volumes of buffer (50 mM Tris-HCl, 120 mN NaCl, 5 mM KCl, 1 mM $CaCl_2$, 1 mM $MgCl_2$, 0.1% L-ascorbic acid, 10 µM pargyline HCl, pH 7.1) using a Polytron homogenizer at setting 5 for three 15-sec bursts. The homogenate is then diluted 4-fold with buffer and centrifuged at 30,000×g for 20 minutes, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

Thirty µL of the homogenate (0.2–0.3 mg protein/sample) are incubated with 0.3 nM $^3$H-spiroperidol (New England Nuclear) and various concentrations of test drug in a final volume of 1 ml of the above buffer for 10 minutes in a 37° C. water bath. At the end of the incubation, 3 ml of cold 50 mM Tris-HC-1, pH 7.7, are added to each tube, and the contents are rapidly vacuum-filtered through Whatman GF/B glass-fiber filters. The filters are then rapidly washed 3 times with 3 ml of the same buffer, placed in scintillation vials, and shaken for 15 minutes with 10 ml of Hydrofluor (National Diagnostics) scintillation cocktail. The vials are then counted in a Packard 460CD scintillation counter.

Specific binding is defined as total binding less binding in the presence of 1 µM (+)butaclamol. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{---Spiroperidol}]}{K_D}}$$

where $K_D = 0.3$ nM for spiroperidol binding

| STANDARD COMPOUNDS: $K_i$ and 95% confidence interval | |
|---|---|
| Haloperidol | 4.0 (3.0–5.6) nM |
| Clozapine | 34 (23–54) nM |
| Fluphenazine | 4.5 (3.6–5.6) nM |
| Sulpiride | 376 (174–5000) nM |

The results of testing of some of the compounds of the invention, and the prior art compound buspirone (8-[4-[4-(2-pyrimidinyl)-1-piperazinyl]butyl]-8-azapiro[4.5]-decane-7,9-dione) in this assay are presented in Table 1.

TABLE 1

| Compound of Example No. | Limbic D-2 Binding ($K_i$nM) |
|---|---|
| Buspirone | 119 |
| 2 | 2000 (no confidence interval) |
| 3 | 24% inhibition at 10 μM |
| 4 | 10% inhibition at 1 μM |
| 5 | 5% inhibition at 1 μM |
| 7 | weak 51% at 10 μM |
| 8 | weak 40% at 10 μM |

The results show that compounds of the invention display a very weak effect, evidencing a low potential for extrapyramidal side effects.

EXAMPLE 11

Another test designed to determine the potential antipsychotic activity of the compounds of the invention is the conditioned avoidance (shelf-jump response) test.

This test is carried out as follows:

Male CD rats (Charles River) maintained at approximately 400–450 gm body weight are used. Previously trained rats are placed in plexiglass experimental chambers divided into two sections; a main chamber ($10\frac{1}{2}'' \times 6\frac{3}{4}'' \times 11\frac{7}{8}''$ high) and an elevated chamber or shelf ($5\frac{7}{8}'' \times 6\frac{7}{8}'' \times 5\frac{3}{4}''$). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock, (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential antipsychotic compounds suppress avoidance responding and increase escape responding.

| STANDARD COMPOUNDS: | |
|---|---|
| | $AB_{50}$ (mg/kg i.p.) |
| Haloperidol | 0.19 |
| Chlorpromazine | 3.69 |
| Clozapine | 6.94 |
| Buspirone | 9.94 |

The results for compounds of this invention in the test are presented in Table 2.

TABLE 2

| Compound of Example No. | $AB_{50}$ mg/kg |
|---|---|
| 2 | 33.34 (i.p.) |
| 3 | 45.80 (i.p.) |

*(i.p.) = intraperitoneally administered drug.

The results show that compounds of the invention are active intraperitoneally in this test.

What is claimed is:

1. A compound having the formula

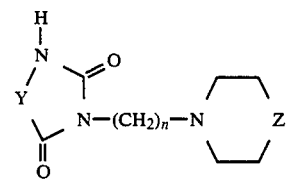

wherein
Y represents

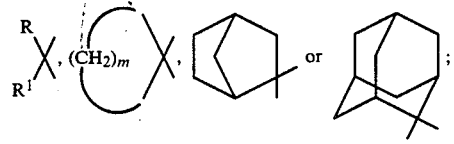

R and $R^1$ are each, independently, hydrogen, lower alkyl, phenyl or naphthyl;
Z is

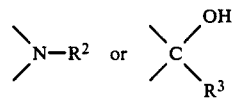

$R^2$ is 2-pyrimidinyl, halopyrimidin-2-yl, 2-pyridinyl, halopyridin-2-yl, cyanopyridin-2-yl, phenyl or phenyl substituted with lower alkyl, halo or trifluoromethyl with the proviso that $R^2$ is phenyl or phenyl substituted with lower alkyl, halo or trifluoromethyl only when Y represents

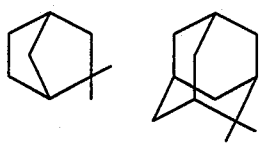

R³ is phenyl or phenyl substituted with halo or trifluoromethyl;

m is 2–7;

n is 4–5; and the pharmacologically acceptable salts thereof.

2. The compound of claim 1, having the name 5,5-diphenyl-3-[4-[4-(2-pyrimidinyl)-4-piperazinyl]butyl]-2,4-imidazolidinedione.

3. The compound of claim 1, having the name 1-[4-[4-(2-pyrimidinyl)-1-piperazinyl]butyl]spiro[bicyclo[2.2.1-]heptane-2,4′-imidazolidine]-2′,5′-dione.

4. The compound of claim 1, having the name 3,[4-[4-(2-pyrimidinyl)-1-piperazinyl]butyl]-2,4-imidazolidinedione.

5. The compound of claim 1, having the name 5,5-pentamethylene-3-[4-[4-(2-pyrimidinyl)-4-piperazinyl]butyl]2,4-imidazolidinedione.

6. The compound of claim 1, having the name 5,5-dimethyl-3-[4-[4-(2-pyrimidinyl)-4-piperazinyl]butyl]-2,4-imidazolidinedione.

7. The compound of claim 1, having the name 5,5-dimethyl-3-[4-[4-(4-chlorophenyl)-4-hydroxy-1-piperidinyl]butyl]-2,4-imidazolidinedione.

8. The compound of claim 1, having the name 5,5-tetramethylene-3-[4-[4-(2-pyrimidinyl)-4-piperazinyl]butyl-2,4-imidazolidinedione.

9. The compound of claim 1, having the name 5,5-tetramethylene-3-[4-[4-(4-chlorophenyl)-4-hydroxy-1-piperidinyl]butyl]-2,4-imidazolidinedione.

10. A compound having the formula

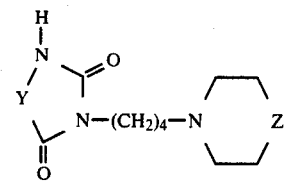

wherein

Y represents

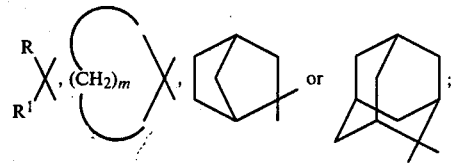

R and R¹ are each, independently, hydrogen, lower alkyl, phenyl or naphthyl;

Z is

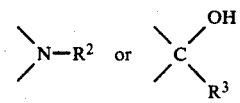

R² is 2-pyrimidinyl, halopyrimidin-2-yl, 2-pyridinyl, halopyridin-2-yl, cyanopyridin-2-yl, phenyl or phenyl substituted with lower alkyl, halo or trifluoromethyl with the proviso that R² is phenyl or phenyl substituted with lower alkyl, halo or trifluoromethyl only when Y represents

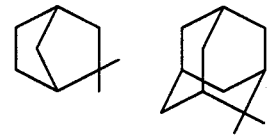

R³ is phenyl or phenyl substituted with halo or trifluoromethyl;

m is 2–7; and the pharmacologically acceptable salts thereof.

* * * * *